United States Patent [19]

Cooper

[11] 4,165,645

[45] Aug. 28, 1979

[54] DRIVE MEANS FOR ORE SAMPLERS AND THE LIKE

[76] Inventor: Harrison R. Cooper, AMF Box 22014, Salt Lake City, Utah 84122

[21] Appl. No.: 930,914

[22] Filed: Aug. 4, 1978

[51] Int. Cl.² ............................................. G01N 1/20
[52] U.S. Cl. ............................................... 73/423 R
[58] Field of Search ......................... 73/421 R, 423 R

[56] References Cited

U.S. PATENT DOCUMENTS

| 2,421,938 | 6/1947 | Held | 73/423 R |
| 2,759,362 | 8/1956 | Pate | 73/423 R |

*Primary Examiner*—S. Clement Swisher
*Attorney, Agent, or Firm*—B. Deon Criddle

[57] ABSTRACT

A drive means for a sampler such as is used to collect ore, slurries or other material discharged from a conveyor or other material transport device. The sampler includes a frame on which a support carriage having a cutter to sample the material as the cutter moves back and forth across the end of the conveyor is mounted. The drive means for moving the sampler carriage includes two closely, spaced, parallel rollers journaled for rotation in the cutter and arranged to move with respect to the frame. A belt attached to one end of the frame passes a first roller, around the outside of a more distant second roller, then back between the rollers, around the first roller and past the second roller to be secured to the frame.

The belt preferably is connected to the frame by a belt adjustment mechanism. Reversible power means are arranged to drive one roller and to thereby reciprocally move the support carriage with respect to the belt and frame.

17 Claims, 3 Drawing Figures

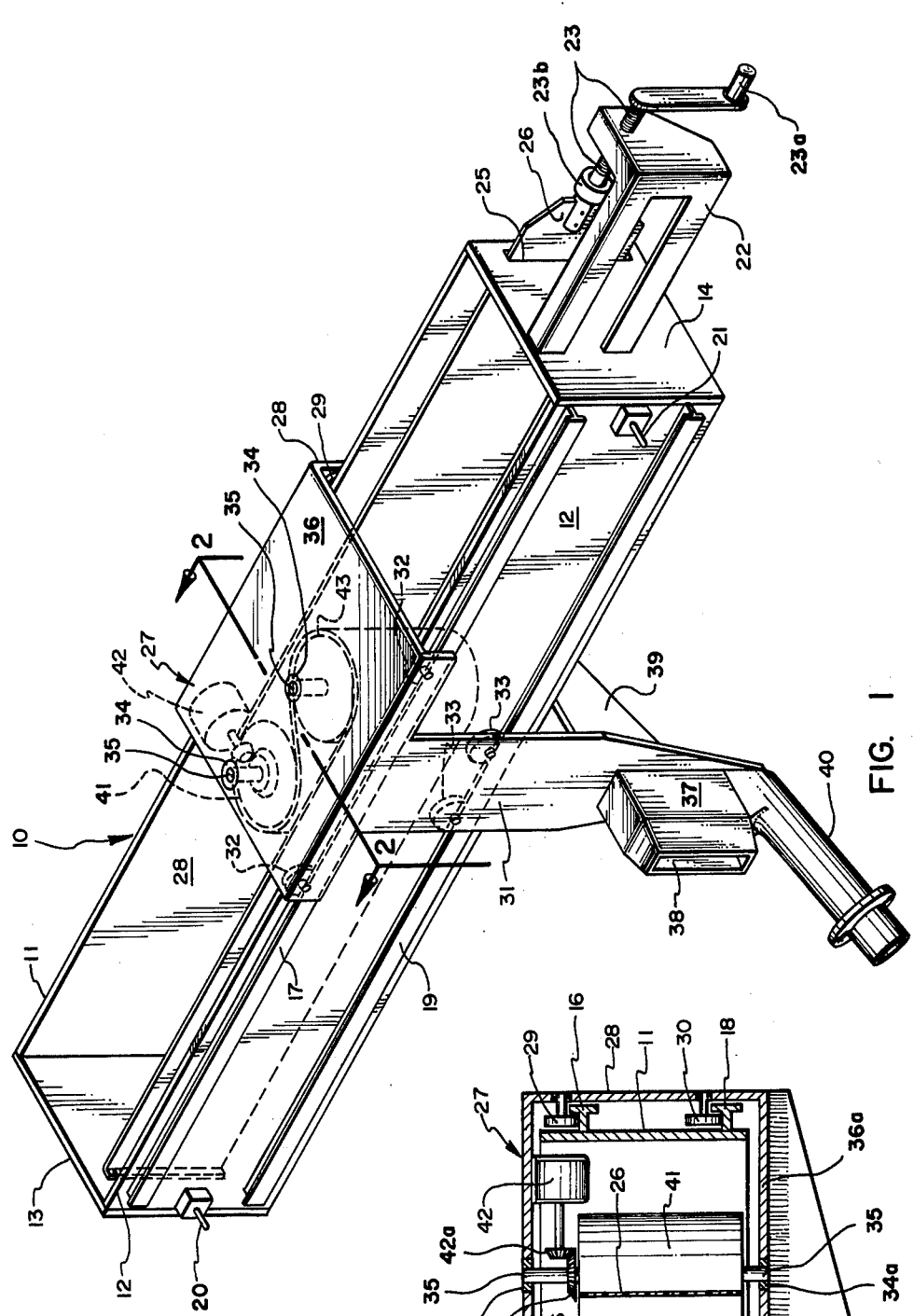
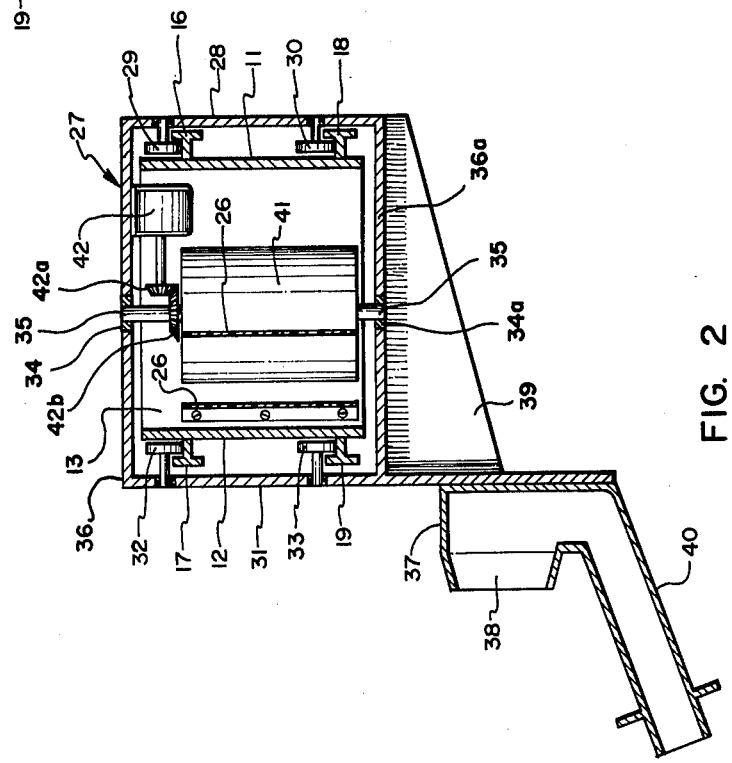

DRIVE MEANS FOR ORE SAMPLERS AND THE LIKE

BRIEF DESCRIPTION OF THE INVENTION

1. Field of the Invention

This invention relates to sampling apparatus and drive means therefor.

2. Prior Art

There are many samplers that are designed to collect samples of ores, concentrates, slurries, vegetable produce, and almost anything that can be moved along a conveyor. Silver et al, for example, disclose apparatus for obtaining samples from a stream of sugar beets in U.S. Pat. Nos. 3,354,512 and 3,373,615, while Phillips teaches a process of sampling cotton as it is being baled in U.S. Patent 3,347,102. Malone teaches a gravel sampling machine in U.S. Pat. No. 3,376,752. A conveyor sampling system is disclosed by Sayre in U.S. Pat. No. 3,253,864. Huntington discloses a multiple stage sampler in U.S. Pat. No. 3,252,328 and other sampling devices in U.S. Pat. Nos. 3,279,210 and 3,387,497. These prior art sampling systems may be quite satisfactory for the particular uses intended, they use various kinds of fluid powered and electric motors and arms, limbs, gears and the like to move a sampling receptacle into and out of the material being sampled. These known devices for moving samplers are not always satisfactory since they do not always work well with materials that tend to foul the operating mechanisms and do not always drive the sampler at constant speed as it is moved into and out of the material being sampled.

SUMMARY OF THE INVENTION

It is a principal object of the present invention to provide a drive mechanism that is particularly adapted for use in driving sampler mechanisms and the like, but that can be used for other reciprocally powered devices as well.

Other objects of the present invention are to provide a sampler using the drive system of the invention that is simple in construction and that can be readily designed to be capable of sampling diverse materials.

Still another object of this invention is to provide a sampler wherein a support carriage is mounted to reciprocate on a frame and wherein a power source is moved with the carriage to drive the carriage and a sample cutter head carried thereby back and forth along a belt stretched the length of the frame.

These and other objects are accomplished in the present invention by means of a roller powered, movable carriage that supports a cutter so that as the carriage is moved across the conveyor at the place where material is being discharged therefrom an accurate and representative sample is "cut" out of the material. The cutter is suspended by a sidewall from a support carriage that moves back and forth on a support frame.

A reversible gear motor is mounted on the carriage and rotates one of a pair of parallel rollers of a dual roller assembly. The dual roller assembly includes the rollers and a belt having its ends fixed at either end of the support frame. The rollers and belt may be either horizontally or vertically placed. The ends of the rollers are journaled for rotation in the carriage. The belt is suspended such that the ends are anchored to opposite ends of the frame and the belt extends between them. The belt is wound around the parallel rollers such that with one end of the belt fastened to one end of the frame the belt extends therefrom past the nearest first roller, around the other second roller, between the rollers, around the first roller, and past the second roller to be anchored at the other end of the frame. Preferably, one end of the belt passes through an end wall of the frame and is fastened to the framework by a belt adjusting mechanism.

In the sampler of the invention as the roller, driven in one direction by the reversible motor, is turned, it moves the entire carriage and both rollers to one end of the frame where a limit switch causes the motor to reverse, and to move the carriage to the other end of the frame where a second limit switch is contacted to again reverse the direction of the motor. When the sampler is positioned at the end of a conveyor from which material is being discharged, the carriage moves back and forth transversely across the end of the conveyor, a representative sample is taken in through the cutter and is discharged through the exit port from which it is collected. While a fixed cutter is here shown it will be apparent that other sample collection devices, such as a scoop that dumps during a cycle of operation could as well be used. The use of rollers and belt, as herein described, simplifies the sampling and provides for a more accurate collection of samples.

THE DRAWINGS

In the drawings:

FIG. 1 is a perspective view of one embodiment of the drive means and a sampler showing the rollers in phantom and with the belt and rollers in a vertical position;

FIG. 2, a transverse sectional view taken along lines 2—2 of FIG. 1; and

FIG. 3, a view like that of FIG. 1, but showing another embodiment of the sampler, with the rollers and belt arranged horizontally and with part of the belt and floor broken away to show the guide rollers.

DETAILED DESCRIPTION

Figure 3:
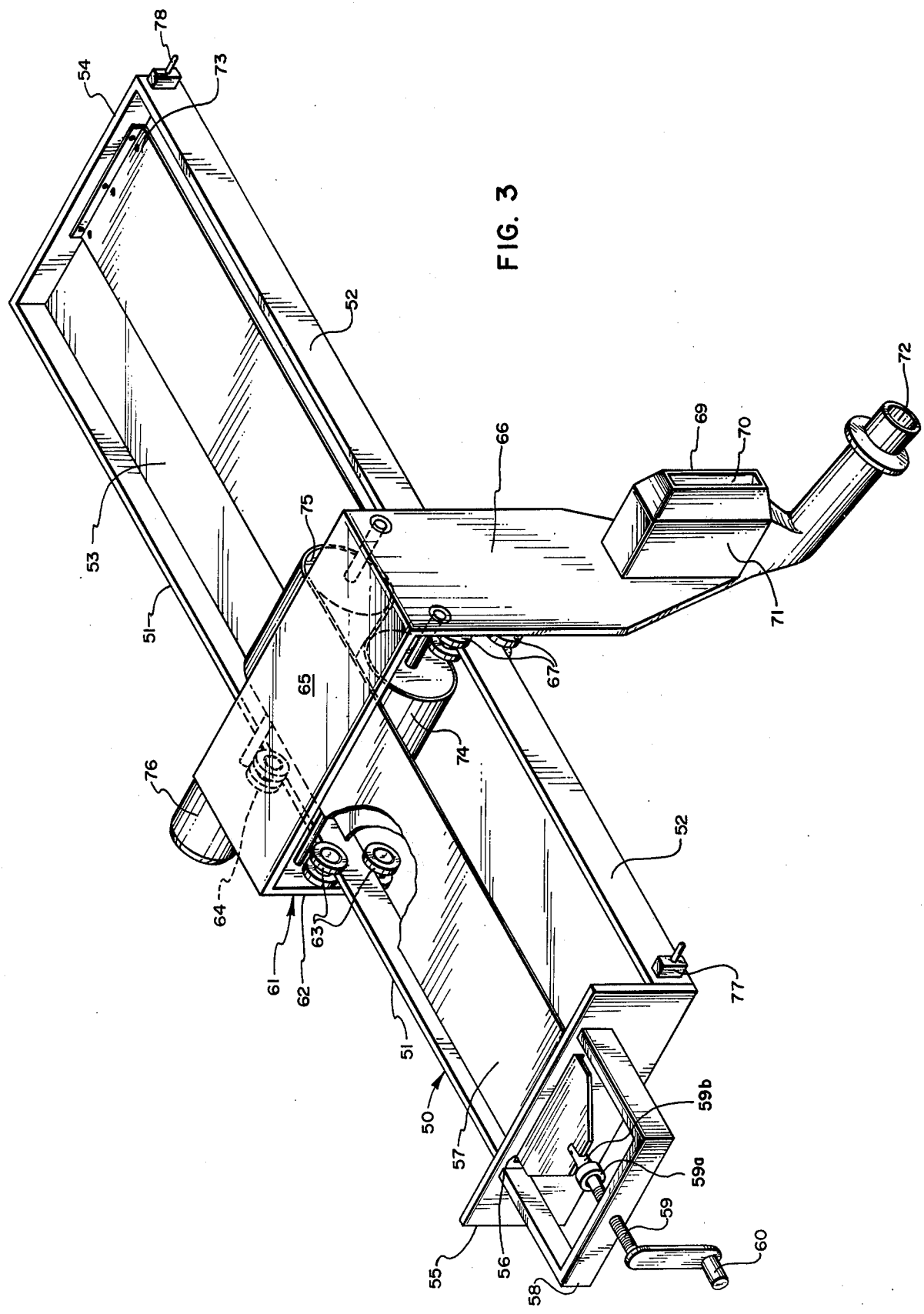

Referring now to the drawing:

As best seen in FIGS. 1 and 2, the sampler 10 of the invention includes a support frame having sidewalls 11 and 12, and ends 13 and 14. Rails 16 and 17 are respectively fixedly attached to the upper outside portion of walls 11 and 12 and rails 18 and 19 are similarly attached to the lower outside portion of the walls 11 and 12.

Limit switches 20 and 21 which are provided to reverse the direction of travel of the sampler, as will be hereinafter described, are respectively mounted at opposite ends of the sidewall 12.

Adjustment means at one end of the support frame includes a threaded bolt 23 having a handle 23a at one end and a universal coupling 23b at its other end connected to a slotted connector 24. End wall 14 has a slot or aperture 25 therein through which a belt 26 may pass to fit into the slot of connector 24.

A support carriage, shown generally at 27, extends a spaced distance over the top of the support frame and down alongside each side thereof. A side 28 of the carriage 27 is adjacent to wall 11 and supports two sets of guide rollers 29 and 30 which respectively ride on rails 16 and 18. The rollers 29 and 30 are journaled in bearings provided in the sidewalls 28. Similarly a side 31 of the carriage 27 is adjacent to sidewall 12 and also supports sets of guide rollers 32 and 33. Each of the guide rollers 32 and 33 is journaled into a sidewall 31. Guide rollers 32 are arranged to roll on rail 17 and guide rollers 33 are arranged to roll on rail 19. The top 36 interconnects the sidewalls 28 and 31 and may carry support bearings 34 in which the upper ends of central shafts 35 of belt rollers to be hereinafter described in detail, may be journaled.

A bottom plate 36a is spaced from the lower edges of sidewalls 11 and 12 and interconnects lower ends of the sides 28 and 31. Bearings 34a, carried by the bottom plate 36a may journal the lower ends of shafts 35.

Sidewall 31 extends downwardly below plate 36a to support an outwardly protruding cutter head 37 that has a cutter opening 38 through which material being sampled is passed, as will be further explained. A web 39 is welded to the downwardly depending portion of sidewall 31 and to the bottom plate 36a. A tube 40 opens into the bottom of the cutter head and extends therefrom to discharge the sample to a desired collection area.

The cutter opening configuration may vary, depending on the characteristics of the material being sampled. For pulverized ore an opening of one by ten inches may be sufficient. When sampling sand, an ore concentrate, a slurry or a liquid, a smaller opening may be required. On the other hand for sampling citrus fruits or sugar beets a larger opening will be required.

With the cutter head 38 suspended beneath the support frame, the guide rollers and the drive means to be hereinafter described for reciprocating the cutter head are out of the path of the material being sampled and are not subjected to wear and corrosion that can result if such structure is placed in the path of material flow.

The drive means of the invention includes the belt 26, a roller 41 driven by a power means such as an electric reversible motor 42 and a freely rotating roller 43. The belt 26 is anchored or secured to end 13 of the support frame by appropriate means such as screws or bolts and is made of flexible, durable material such as nylon, rubber reinforced with cordage made from fibers of steel or other metals or synthetics such as various nylons, polycarbonates, graphite fibers and the like.

As shown in FIG. 1, the belt 26 extends from end wall 13 along the sidewall 12, then around the roller 43, reversely around the roller 41, and alongside sidewall 11 to the slotted connector 24. Handle 23a is then rotated to position connector 24 and to tension the belt 26.

In operation of the drive means and sampler embodiment of FIG. 1, the motor 42 is actuated to drive the roller 41. As the roller 41 is driven in a clockwise rotational direction, as viewed in FIG. 1, the roller 41 pulls material of belt 26 from around roller 43 and moves to the left. When the roller 41 moves it carries the support frame and motor until the support frame engages the limit switch 22 to reverse the direction of rotation of the motor. When the motor is reversed to drive the roller 41 in a reverse direction, i.e. counter-clockwise as shown in FIG. 1, the frictional engagement of roller 41, the belt passing between the rollers and roller 43 rotates the roller 43 in a clockwise direction. This movement pulls the belt around roller 41 as the rollers and support frame carried thereby are moved to the right. The movement to the right, as viewed in FIG. 1, will continue until the limit switch 21 is contacted by the support frame and the direction of rotation of motor 42 is again reversed. The sample cutter head picks up samples and deposits them as the support frame traverses back and forth transversely through a stream of material to be sampled between the limit switches. While the motor 42 is shown as driving roller 41 through spur gears 42a and 42b, it will be apparent that the motor can be directly used, if desired. It should also be apparent that hydraulic motors, combustion engines or other drive means can be used in place of the electric motor 42, if so desired.

The speed of reciprocation of the cutter head may be regulated as desired, and it will be apparent that the cutter head may be changed to accommodate samples of different kinds of material.

Another embodiment of the invention is shown in FIG. 3. As shown, a sampler 50 has two side rails 51 and 52 and a floor 53 that is illustrated as being partially broken away to show components therebeneath. End walls 54 and 55 are attached to the side rails and floor. End wall 55 projects higher than end wall 54 and has a slot 56 formed therein through which a belt 57 may extend. A belt tensioner, including a frame 58 that is fixed to end wall 55 has a threaded bolt 59 with one end attached by a universal coupling 59a to a slotted connector 59b to one end of the belt 57. The other end of bolt 59 extends through the frame 58 and has a handle 60 thereon.

A support carriage 61 is provided. The carriage is similar to the carriage shown in FIG. 1. A sidewall 62 of the carriage moves adjacent to the rail 51 of a support frame. Two sets of idler rollers 63 and 64 (only one of which is shown) are carried by the sidewall 62, with one roller of each set being arranged to roll on the top of rail 51 and the other roller of each set being arranged to roll on the bottom of rail 51. A top plate 65 of the carriage interconnects the sidewall 62 and a sidewall 66 that moves adjacent to rail 52. The sidewall 66 carries two sets of rollers corresponding to the rollers carried by sidewall 62. Only the set 67 of rollers carried by sidewall 66 is shown but it should be understood that another set is similarly arranged.

A cutter head 69 having a cutter opening 70, cutter body 71 and sample discharge tube 72 all of which operate in the manner heretofore described, is provided at the lower portion of sidewall 66.

The control mechanism of the embodiment of FIG. 3 is essentially the same as in that disclosed in connection with the embodiment of FIG. 1. In this embodiment, however, the rollers are horizontal instead of being vertical. The belt 57 has one end 73 anchored to end wall 54, extends close to floor 53, around freely rotating roller 74, reversely around driven roller 75 and through slot 56. The other end of the belt is then attached to a slotted connector 59a on one end of a threaded bolt 59 arranged in the same manner as the threaded bolt 23, previously described, as part of a belt tensioner. Driven roller 75 is drivingly connected to a drive means such as the electric motor 76. Upon actuation the motor causes the driven roller 75 to rotate and to either push or pull the freely rotating roller 74, which moves in the same direction but rotates in an opposite direction as the driven roller. When one end of the frame support is reached by the carriage a limit switch 77 reverses the motor and the carriage operates in the opposite direction until limit switch 78 is reached. The cycle is repeated until sufficient sample has been collected.

As in the previously described embodiment, the sampler head can be any desired size and the cutter opening and size may be varied to accommodate the sample being collected.

Although preferred embodiments of the invention have been disclosed, it is to be understood that departures may be made therefrom without departing from the scope of the invention which is not to be limited to the details disclosed, but is to be accorded the full scope of the claims so as to include any and all equivalent devices and structure.

I claim:

1. A drive means for ore samplers and the like, said drive means comprising
   a support frame having spaced apart ends;
   a belt having its opposite ends anchored to the spaced apart ends of the support frame;
   a pair of closely spaced parallel rollers;
   means journalling said rollers for movement along the support frame, said means being movable with said rollers along the support frame and positioning said rollers whereby the belt extends from one fixed end past one of said rollers, around the second roller, between the rollers, and around the first roller to the other fixed end; and
   means for rotationally driving one of said rollers.

2. A drive means as in claim 1, wherein
   the support frame has guide rails thereon and wherein the means journalling the rollers comprises a carriage having rollers arranged to roll along said guide rails.

3. A drive means as in claim 2, wherein
   the means for rotationally driving one of said rollers comprises a motor carried by the carriage.

4. Sampler apparatus for sampling materials discharged from conveyor systems and the like comprising
   a support frame having spaced apart ends;
   a sampler carriage mounted for movement on said support frame, said carriage carrying a sampling cutter having a cutter opening and means for discharging a sample collected through said cutter opening;
   a drive means for moving said sampler carriage with respect to said support frame, said drive means comprising
      a belt having its opposite ends anchored to the spaced apart ends of the support frame;
      a pair of closely spaced parallel rollers at least one of which is secured to the sampler carriage and movable along the support frame with the carriage, said rollers being positioned such that the belt extends from one fixed end of frame past one of said rollers, around the second roller, between the rollers, and around the first roller to the other fixed end; and
      a motor carried by the support carriage and arranged to turn one of said rollers.

5. Sampler apparatus as in claim 4, further including means at each of the spaced apart ends for reversing the motor when the carriage reaches said ends.

6. Sampler apparatus as in claim 5, wherein
   the motor is an electric motor and the means at each of the spaced apart ends for reversing the motor comprise switches electrically connected to the motor.

7. Sampler apparatus as in claim 4, further including means to adjustably tension said belt.

8. Sampler apparatus as in claim 4, wherein
   the sampler carriage includes a sampler sidewall extending downwardly below the support frame and wherein the cutter head is carried by a portion of the sampler sidewall below the support frame.

9. Sampler apparatus as in claim 8, wherein the rollers extend parallel to the downwardly extending sampler sidewall.

10. Sampler apparatus as in claim 8, wherein the rollers extend transversely to the downwardly extending sampler sidewall.

11. A sampling apparatus comprising
   a support frame having a pair of spaced apart ends;
   a support carriage reciprocably mounted on said support frame, said carriage includes a sidewall, a top, and an opposing sampling sidewall extending downwardly to support an outwardly facing sampling head having a cutter opening and a discharge tube projecting downwardly therefrom;
   drive means for reciprocating the sampler carriage along the support frame, said drive means including a belt having its opposite ends respectively attached to the spaced apart ends of the support frame, a pair of parallel, closely spaced rollers at least one of which is secured to said sampler carriage and mounted with respect to said belt such that the belt extends from one end of the support frame, past a first one of said rollers, around said first roller, between said rollers, reversely around the other of said rollers, and past the first roller to the other end of the support;
   a limit switch near each end of the support frame; and
   a motor operated by said limit switches and connected to one of said rollers such that when the motor is actuated the roller connected to said motor will rotate and move the sampler carriage toward one end of the support structure, with the other roller being rotated through the belt in a direction opposite to that of the driven roller until the limit switch at one end of said support frame is reached whereupon the motor is reversed, thereby reversing rotation of the rollers and moving the support carriage in an opposite direction until the limit switch at the other end of the support structure is reached to thereby cause the drive means to again reverse, said reciprocal movements being continued to move the sampling head back and forth through material being sampled.

12. Sampling apparatus as in claim 11, further including
   an adjustment frame extending from one end of the support frame and having a bolt threaded therethrough one end of said bolt having a handle thereon and the other end being secured to one end of the belt, whereby rotation of the handle will cause the tension on the belt to be adjusted.

13. A sampling apparatus according to claim 12, wherein the motor is an electric motor.

14. A sampling apparatus according to claim 12, wherein the rollers are arranged vertically.

15. A sampling apparatus according to claim 14, further including
   rails interconnecting the ends of the support frame; and
   guide rollers on the support carriage engaging the rails to roll thereon.

16. A sampling apparatus according to claim 12, wherein
   the rollers are arranged horizontally.

17. A sampling apparatus according to claim 16, further including
   rails interconnecting the ends of the support frame; and
   guide rollers carried by the support carriage and engaging both the top and bottom of said rails to be movable therealong.

* * * * *